Figure 1:
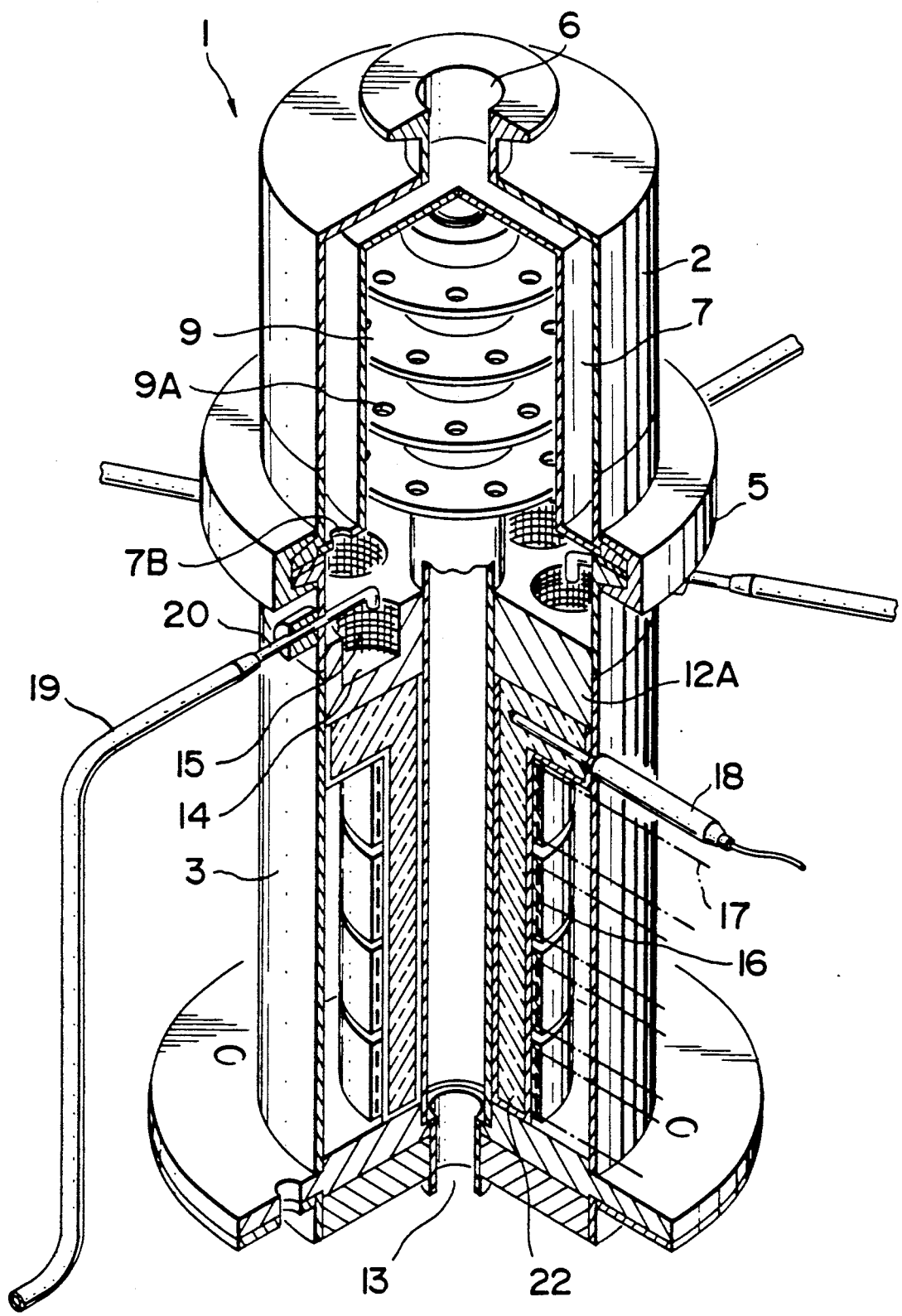

United States Patent [19]
Shibauchi et al.

[11] Patent Number: 5,078,976
[45] Date of Patent: Jan. 7, 1992

[54] DISINFECTANT VAPORIZING APPARATUS

[75] Inventors: Yoshito Shibauchi, Kawagoe; Koichi Hatanaka, Sayama; Tasuo Tanaka, Sayama, all of Japan

[73] Assignee: Snow Brand Milk Products Co., Ltd., Hokkaido, Japan

[21] Appl. No.: 285,267

[22] Filed: Dec. 16, 1988

[30] Foreign Application Priority Data

Dec. 23, 1987 [JP] Japan .................. 62-326287

[51] Int. Cl.⁵ .............................................. A61L 2/20
[52] U.S. Cl. ...................................... 422/298; 43/129;
  122/491; 239/136; 261/DIG. 65; 392/395;
  392/399; 422/29; 422/38; 422/306
[58] Field of Search ............ 422/28, 29, 38, 298,
  422/306, 307; 261/DIG. 65; 43/125, 129-130;
  122/34, 491; 219/271-273, 275, 276; 239/38,
  44, 57, 136; 392/386, 395, 399

[56] References Cited

U.S. PATENT DOCUMENTS

| | | | |
|---|---|---|---|
| 468,048 | 2/1892 | Rayner | 122/491 X |
| 604,598 | 5/1898 | Boswell . | |
| 1,410,164 | 3/1922 | Carroll | 422/306 |
| 2,047,973 | 7/1936 | Lawton | 239/38 X |
| 2,262,327 | 11/1941 | McKinnon | 239/44 |
| 4,003,967 | 1/1977 | Potvin | 219/276 X |
| 4,190,052 | 2/1980 | McCarthy | 219/273 X |
| 4,631,173 | 12/1986 | Müller et al. | 422/28 |

FOREIGN PATENT DOCUMENTS 0708729  4/1930  France .................. 219/276

Primary Examiner—Robert J. Warden
Assistant Examiner—Amalia Santiago
Attorney, Agent, or Firm—Griffin Branigan & Butler

[57] ABSTRACT

A disinfectant vaporizing apparatus for dropwise flowing a disinfectant liquid on a heating unit so as to provide a uniform disinfection gas on a surface of a material to be sterilized, characterized in that at least one supply port for supplying heated carrier gas at a high temperature is provided in a vaporization chamber for the disinfectant liquid. A vaporization part is provided with a plurality of cavities on an upper surface thereof and at least one dropping nozzle is provided above each cavity, wherein the disinfection gas carried by the heated carrier gas is applied on a surface of a material to be sterilized through a droplet splash removing apparatus. The droplet splash removing apparatus has a series of vertically, spaced-apart shield plates with staggered holes therein through which the vaporized disinfectant and carrier gas pass and entrained droplets of disinfectant liquid are removed.

11 Claims, 3 Drawing Sheets

DISINFECTANT VAPORIZING APPARATUS

BACKGROUND OF THE INVENTION

The present invention relates to an apparatus for vaporizing a disinfectant by dropping it on a heating element. The apparatus is applied to such a technical field that, when a packing material including a container or the like is sterilized or disinfected by using disinfection gas, the material to be sterilized is sterilized by dropping a disinfection liquid on the heating element to vaporize the liquid, introducing the vaporized gas, with a heated carrier gas, to the surface of the material to be sterilized and condensing the carried disinfection gas on the surface of the material to be sterilized.

Heretofore, there is disclosed in the above-mentioned technical field a method using hydrogen peroxide as a disinfection gas and a spray vaporization method of the liquid. According to said spray vaporization method, it is necessary to provide a system for pressurizing hydrogen peroxide and a spray chamber. Some trouble in such a process, such as blinding of nozzles and hunting of spray, is likely to occur.

Therefore, the method of Japanese Patent Application 174235/86 has been proposed by the present applicant. The application adopts a drop vaporization method in which hydrogen peroxide is vaporized by dropping it on a board heating type or a falling heating type.

That is, according to the board heating type unit, a stainless net is provided on a heat transfer block as an evaporation surface, a blow-off opening for heated carrier air is provided above the evaporation surface parallel to the surface of the heat transfer block, the heated air is blown from the opening to promote the evaporation of hydrogen peroxide and the hydrogen peroxide gas is carried to the material to be sterilized. A filter means is provided adjacent to the outlet of the vaporization chamber so as to prevent droplet splashes of hydrogen peroxide caused by flow increase of the carrier air or by the spheroidal phenomenon of the liquid hydrogen peroxide on the heated surface from being carried with the hydrogen peroxide gas.

Referring now to the falling heating type unit, a stainless net is provided as a vaporization surface in a vertical double heat pipe, a blow-off opening for heated carrier air is provided below said double heat pipes and the heated air is blown up along the interval between the double heat pipes. Other features are substantially same as those of the board heating type unit previously explained.

In general, the drop vaporization method presents some difficulties in controlling the rate of supply of the material to be sterilized to the sterilizing apparatus and the drying conditions of the material to be sterilized. That is, if the droplet splashes of hydrogen peroxide are entrained with the hydrogen peroxide gas, the gas density becomes uneven, resulting in uneven sterilization of the surface to be sterilized. In order to overcome the above disadvantages, there should be provided a means for controlling the rate of supply of the material to be sterilized in accordance with the gas density or a means for controlling the drying temperature, the drying velocity or the like in the drying process of the material to be sterilized. With this, however, the control of the sterilization becomes complex.

The above disadvantages have not yet been overcome by the apparatus for vaporizing hydrogen peroxide liquid by dropping it on the heating unit, as disclosed in said Japanese Patent Application 17425/86. That is, according to said Japanese Patent Application 17425/86, because the board heating type unit thereof has a stainless net provided above the heat transfer block in the shape of the plate as the evaporation surface, the area to be heated extends horizontally and therefore uneven heating and thermo difference in some parts of the heated surfaces occur. With this, the gas density also becomes uneven and uniform supply of hydrogen peroxide as the disinfection cannot be conducted.

Further, the hydrogen peroxide which is not evaporized because of the uneven heating often accumulates at the bottom of the apparatus. Further, there also occurs large heating loss caused by the large heating area. Additionally, the prior filter means for preventing the drop splashes of hydrogen peroxide from accompanying the hydrogen peroxide gas is not sufficient to make the vaporized hydrogen peroxide gas uniform.

Further, according to the falling heating type disclosed in said Japanese Patent Application 174235/86, the heated surface is also large, and heat spreads vertically, and therefore it leaves the same disadvantages as those of the board heating type unit.

SUMMARY OF THE INVENTION

Accordingly, the object of the present invention is to provide a disinfectant vaporizing apparatus for dropping disinfection liquid on a heating unit and for providing uniform disinfection gas on a surface of a material to be sterilized. According to the present invention, there is provided a disinfectant vaporizing apparatus which is characterized in that at least one supply port for supplying heated carrier gas at high temperature is provided in a vaporization chamber 8 for the disinfectant in which at least one dished vaporization part 14 is provided on an upper surface of an evaporation unit 12 and at least one dropping nozzle is provided thereabove, respectively, wherein the disinfection gas carried by the heated carrier gas is applied on a surface of a material to be sterilized through a droplet splash removing apparatus.

The droplet splash removing apparatus is not limited to the disclosed shield plates or filter means only and any means which can remove droplet of the disinfection liquid can be used. For the disinfectant, liquid disinfectant such as hydrogen peroxide, alcohol or the like can be used.

For the heated carrier gas, not only hot air but also inlet gas mixed gas of inlet gas and air or the like can be used.

The operation of the disinfectant vaporizing apparatus according to the present invention will be described hereinafter based on FIG. 2. The pre-heated carrier gas at high temperature is applied to the disinfectant vaporizing apparatus from a inlet port 6. The heated carrier gas moves along the interval between an upper outer cylinder 2 and an inner cylinder 7 to reach an evaporation chamber 8 through an opening 7B (see FIG. 1).

Figure 2:
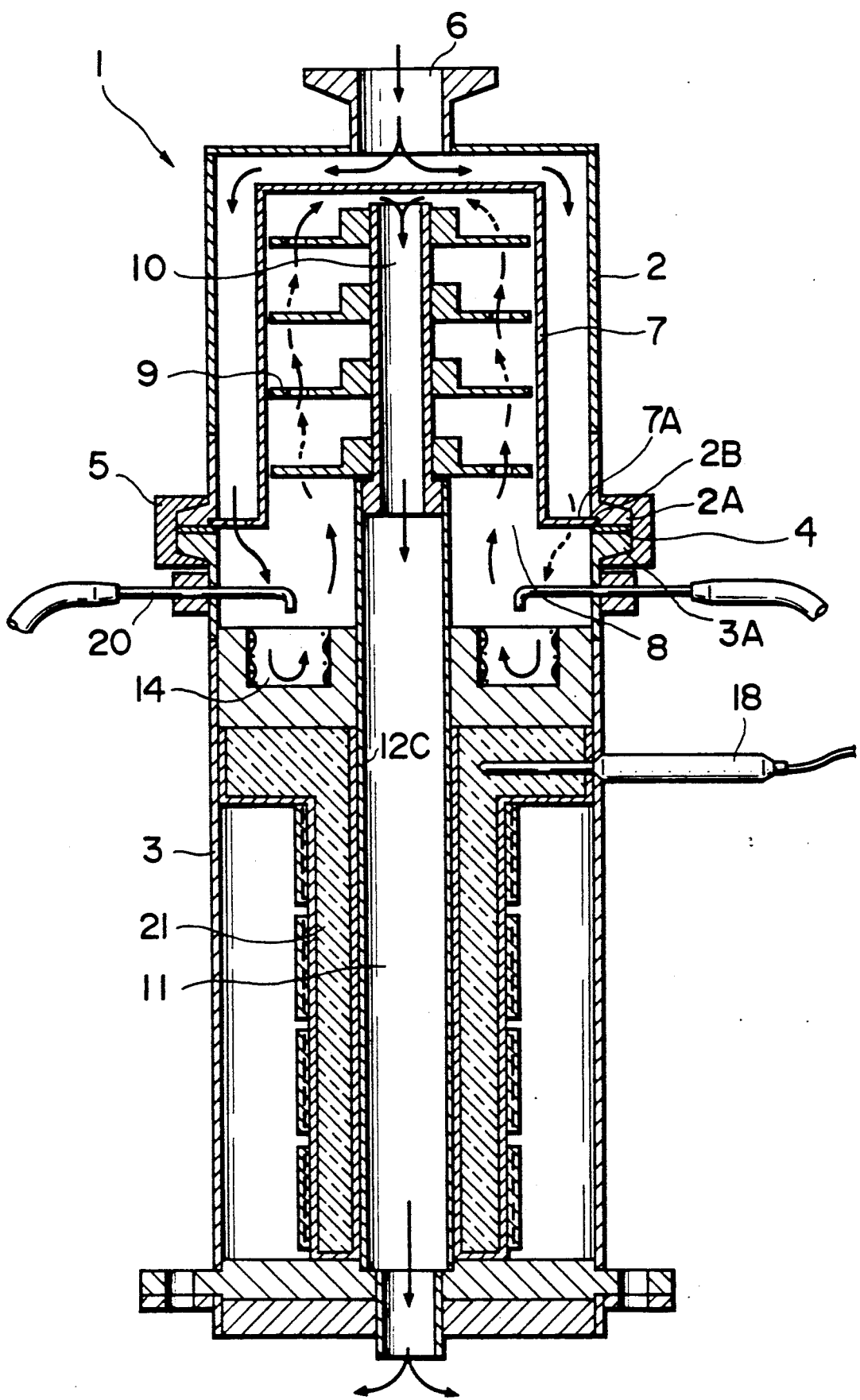

On the other hand, disinfectant applied from a quantitative supply apparatus is dropped on a dished vaporization part from a dropping nozzle 20 through a supply tube 19 (see FIG. 1). An evaporation unit 12 (see FIG. 3) is heated by a heater means 16. Because the dished vaporization part is heated by heat transmitted through the outer or inner surface of the evaporation unit 12, the drops of the disinfectant dropped on the dished vaporization part is heated to evaporate.

Figure 4:
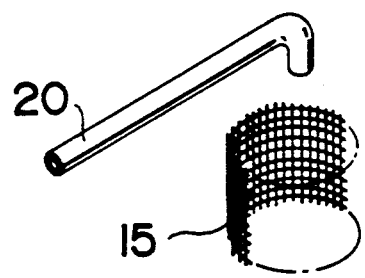
Figure 4:
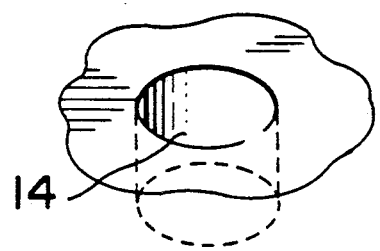

When the heated temperature of the disinfectant drops exceeds a predetermined (known) temperature, a membrane forms between the drops and the evaporation surface, which causes droplet particles to float, the coefficient of heat transfer decreases, and the evaporation time increases, namely spheroidal phenomenon occurs. Therefore, a cylindrical net 15 may be provided about the walls of the dished, for example concaved, cylindrical evaporation part 14. With this, the drops are broken into parts by the cylindrical net 15, resulting in shorter evaporation time.

Disinfection gas, which has been heated and vaporized on the dished evaporation part, is carried with heated carrier gas to an opening of an upper inner tube 10 through a droplet splash removing apparatus.

The droplet splash removing apparatus may be provided with plural shield disks 9 arranged to form stairs, which disks are provided with a plurality of holes 9A (see FIG. 1). The holes 9A which are adjacent to each other on a shield disk 9 should be arranged staggeringly, and additionally the holes provided on shield disks 9 which are adjacent to each other should have the holes arranged so that holes in adjacent disks do not overlap each other in the vertical direction (as shown in FIG. 1). Then the mixture of the disinfection gas and the heated carrier gas will rise snakingly or swirlingly. The dropwise or splashwise disinfectant liquid cannot rise therewith and combine into large drops, which would fall back into the apparatus. Further, since the mixture of the disinfection gas and the heated carrier gas is snaked or swirled, the resulting mixed gas has a uniform density.

The mixture of the disinfection gas and the heated carrier gas carried to the opening of the upper inner tube 10 from the drop splash removing apparatus descends through the upper inner tube 10 and the lower inner tube 11 to be supplied to the disinfection apparatus directly from an exhaust port 13 or through an induction pipe (not shown).

The apparatus according to the present invention has the following advantages. Since the surface area of the evaporation part is small compared with the well-known unit, there are no uneven heating, no accumulation of the disinfectant such as hydrogen peroxide at the bottom of the evaporation part and no heating loss.

Further, since the surface area of the evaporation part is small, control of the temperature of the evaporation part has become easier.

Additionally, since, when the surface area of the evaporation part is small and shield plates are provided above the evaporation part as a drop splash removing apparatus, the dropwise or splashwise disinfectant liquid cannot rise and combine into large drops, resulting in falling thereof, and, hence, uniform disinfection gas accompanied with the heated carrier gas can be supplied on the surface of the material to be sterilized.

Furthermore, the apparatus is compact enough as an evaporation means, and it can easily be demounted in respect to maintenance and therefore has considerable economical effect

BRIEF DESCRIPTION OF THE DRAWINGS

The above and the other objects of the invention will be seen by reference to the description taken in connection with the accompanying drawings, in which:

FIG. 1 is a perspective view including partial sectional view showing one embodiment according to the present invention using hydrogen peroxide as a disinfectant, FIG. 2 is a sectional view showing the operation of the apparatus of FIG. 1, FIG. 3 is a partial view of the evaporation unit, and FIG. 4 is an explanational view with respect to the concaved cylindrical evaporation part.

DESCRIPTION OF THE INVENTION

Referring to the drawings, as shown in FIG. 1, reference numeral 1 is a hydrogen peroxide vaporizing apparatus comprising an upper outer cylinder 2 and a lower outer cylinder 3. A flange 2A is provided in the lower surface of the upper outer cylinder 2 and a flange 3A is provided in the upper surface of the lower outer cylinder 3. A packing 4 is provided between the flanges. A ring 5 having concaved cross section is removably mounted to cover the flanges. An inlet port 6 is arranged on the upper portion of the upper outer cylinder 2. An inner cylinder 7 is provided inside the upper outer cylinder 2, which inner cylinder 7 has a flange 7A at the lower portion thereof and the periphery of the flange 7A is arranged to fit between a cutout portion 2B of the flange 2A and the inner periphery surface of the flange 3A. An opening 7B (see FIG. 1) is provided in the flange 7A, and with this, the carrier hot air is discharged to a vaporization chamber 8. The vaporization chamber 8 is determined by the flange 7A, an evaporation unit 12 and the lower outer cylinder 3. The profile of the vaporization chamber of the present invention is not limited to the above construction. Shield disks 9 are provided along an upper inner tub e10 inside the inner cylinder 7 and a stairs construction is formed by the plural shield disks 9. A plurality of holes 9A are provided on the shield disks 9, which holes adjacent to each other are arranged staggeringly and the holes of a shield disk are arranged so as to not overlap other holes of an adjacent disk in the vertical direction, i.e. the holes in a shield plate are not in vertical alignment with hole sin an adjacent shield plate. The arrangement of the plural holes adjacent to each other and the arrangement of the holes of the plural shield disks are not limited to the above described arrangement, and any construction in which the mixture of the hydrogen peroxide gas and the carrier hot air can rise snakingly or swirlingly can be applied. Further, the shield disk is not limited to the disk-like shield. The drop splash removing apparatus is not limited to the construction in which the plural shield plates, provided with the plural holes, are arranged to form stairs and any means for removing the drops of the disinfection liquid can be used and not only the shield plate but also a filter means or an agitation wing means or the like can be also applied.

The upper portion of the upper inner tube 10 opens to the upper inner surface of the inner cylinder 7 and a lower inner tube 11 is connected with the lower portion of the upper inner tube 10. The lower inner tube 11 passes through an inner path 12C of the evaporation unit and an exhaust port 13 for the disinfectant gas and hot carrier gas is provided in the lower portion of the lower inner tube 11.

On the other hand, the evaporation unit 12 is provided inside the lower outer cylinder 3, which evaporation unit 12 comprising an upper cylinder portion 12A and a lower cylinder portion 12B (see FIG. 3) having a diameter less than that of the upper cylinder portion 12A and the inner path 12C is vertically provided in the inner side of the upper cylinder portion 12A and the lower cylinder portion 12B. Plural concaved cylindrical vaporization parts 14 are provided on the upper surface of the cylindrical portion 12A. As shown in FIG. 4, a cylindrical net 15 is provided about the walls of the cancaved cylindrical vaporization part 14. The vaporization part 14 is not limited to the concaved cylindrical unit, and any dished unit can be applied. Plural heaters 16 are arranged to form stages in the lower cylinder portion 12B and lead wires 17 are connected with the heater 16. A space 22 is provided below the concaved cylindrical vaporization part 14 inside the evaporation unit 12 and a thermo sensor 18 is inserted to the upper portion thereof from the outside of the lower outer cylinder 3.

Figure 3:
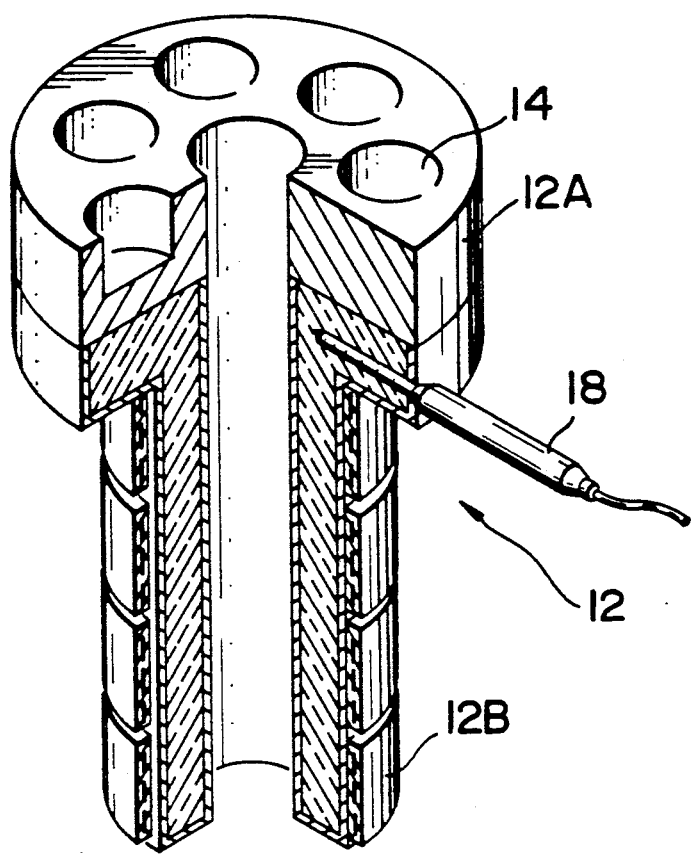

A vaporization condition can be measured by the thermo sensor 18 which is substantially equal to the condition of the concaved cylindrical vaporization part 14. The part of the space 22 belonging to the upper cylinder portion 12A can be filled with a filler having good coefficient of thermal conductivity and also it can be integrally molded with the same material as the evaporation unit 12. In this case, as shown in FIG. 3, the space of the upper cylinder portion 12A is used only as a hole for the thermo sensor. In the part of the space 22 belonging to the lower cylinder portion 12B, heat insulating material 21 is filled.

The hydrogen peroxide liquid is supplied from a quantitative apparatus (not shown) through plural supply tubes 19. As shown in FIG. 4, dropping nozzles 20 are connected with the end of the supply tube 19 and each dropping nozzle passes through the lower outer cylinder 3 and is turned down above the concaved cylindrical vaporization part 14.

While the invention has been particularly shown and described with reference to preferred embodiment thereof, it will be understood by those skilled in the art that the foregoing and other changes in form and details can be made therein without departing from the spirit and scope of the invention.

We claim:

1. An apparatus for vaporizing a disinfectant solution, comprising:
   (a) a generally vertically disposed outer shield having a closed upper end;
   (b) a generally vertically disposed inner shell having a closed upper end, an opened lower end and contained within said outer shell such that an annular space is provided between said outer shell and said inner shell;
   (c) an elongated inner tube generally vertically disposed within said inner shell with an upper end of said tube terminating near said closed upper end of the inner shell;
   (d) a filter means generally laterally disposed about said inner tube and within said inner shell;
   (e) a vaporization part disposed below said filter means and containing a plurality of cavities therein;
   (f) heating means for heating said vaporization part and said cavities above the vaporization temperature of the disinfectant solution;
   (g) a nozzle disposed above each said cavity for dropwise flowing the disinfectant solution into said cavities and causing immediate vaporization thereof;
   (h) a carrier gas inlet port disposed through said closed end of the outer shell; and
   (i) moving means for moving a carrier gas through said inlet port, downwardly through said space between said outer shell and said inner shell, across said vaporization part and the cavities therein, upwardly into said inner shell and through said filter means, into said upper end of said inner tube, and downwardly through said inner tube, through an exhaust port and out of said apparatus.

2. The apparatus of claim 1 wherein the filter means is a plurality of vertically spaced apart shield plates, and each of said shield plates has a plurality of spaced apart holes therethrough.

3. The apparatus of claim 2 where the holes in each shield plate are staggered with respect to each other.

4. The apparatus of claim 2 wherein the holes in a shield plate are not in vertical alignment with holes in an adjacent shield plate.

5. The apparatus of claim 1 wherein said cavities have a concave cylindrical shape and cylindrical net is disposed about the cylindrical portion thereof.

6. The apparatus of claim 1 wherein said cavities are dish shaped.

7. The apparatus of claim 1 wherein said inner tube is generally centrally disposed within said inner shell.

8. The apparatus of claim 1 wherein said heating means is disposed beneath said vaporization part and a lower end of the inner tube extends through said heating means.

9. The apparatus of claim 6 wherein said heating means has an elongated lower portion and an extension of said lower end of the inner tube extends through said elongated lower portion.

10. The apparatus of claim 1 wherein the heating means is electrically heated.

11. The apparatus of claim 1 wherein a thermo sensor is disposed in said vaporization part for maintaining the temperature of the vaporization part above the vaporization temperature of the disinfecting solution.

* * * * *